(12) United States Patent
Govari

(10) Patent No.: US 11,998,265 B2
(45) Date of Patent: Jun. 4, 2024

(54) RESPIRATION CONTROL DURING CARDIAC ABLATION

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 837 days.

(21) Appl. No.: 16/724,683

(22) Filed: Dec. 23, 2019

(65) Prior Publication Data

US 2021/0186602 A1 Jun. 24, 2021

(51) Int. Cl.
| | |
|---|---|
| *A61B 18/12* | (2006.01) |
| *A61B 5/00* | (2006.01) |
| *A61B 5/06* | (2006.01) |
| *A61B 18/14* | (2006.01) |
| *A61B 18/00* | (2006.01) |

(52) U.S. Cl.
CPC .......... *A61B 18/1492* (2013.01); *A61B 5/065* (2013.01); *A61B 5/6853* (2013.01); *A61B 5/6858* (2013.01); *A61B 2018/00351* (2013.01); *A61B 2018/00577* (2013.01)

(58) Field of Classification Search
CPC ... A61B 18/1492; A61B 5/065; A61B 5/6853; A61B 5/6858; A61B 2018/00351; A61B 2018/00577; A61B 18/12; A61B 18/1206; A61B 18/1233; A61B 18/14; A61B 18/1402; A61B 2018/00708; A61B 2018/00642; A61B 2018/00839; A61B 2018/00357; A61B 2018/00613; A61B 2018/00761; A61B 2018/00827; A61B 2018/00875; A61B 2018/0022; A61M 16/00; A61M 2202/0208

USPC ...... 606/32, 34, 40–42, 49; 607/98, 99, 113, 607/115, 116, 119, 122

See application file for complete search history.

(56) References Cited

U.S. PATENT DOCUMENTS

| | | | |
|---|---|---|---|
| 5,391,199 A | 2/1995 | Ben Haim | |
| 6,239,724 B1 | 5/2001 | Doron | |
| 6,296,630 B1 * | 10/2001 | Altman | A61M 25/0084 604/508 |
| 6,332,089 B1 | 12/2001 | Acker | |
| 6,484,118 B1 | 11/2002 | Govari | |

(Continued)

FOREIGN PATENT DOCUMENTS

| | | |
|---|---|---|
| WO | WO1996005768 A1 | 2/1996 |
| WO | WO2004082729 A2 | 9/2004 |
| WO | WO-2017132768 A1 * | 8/2017 ......... A61B 18/1492 |

OTHER PUBLICATIONS

European Search Report for corresponding EPA No. 20216381.2 dated May 20, 2021.

*Primary Examiner* — Thomas A Giuliani
(74) *Attorney, Agent, or Firm* — Dergosits & Noah LLP; Todd A. Noah

(57) ABSTRACT

A method for invasive cardiac treatment, including inserting a catheter via a transvascular route into a beating heart of a patient who is anesthetically paralyzed and intubated for ventilation, and, after inserting the catheter, temporarily halting ventilation of the patient. The method includes moving the catheter between a plurality of locations of myocardial tissue of the heart while the ventilation is halted; and ablating the myocardial tissue of the heart at the plurality of locations while the ventilation is halted.

18 Claims, 3 Drawing Sheets

(56) References Cited

U.S. PATENT DOCUMENTS

| | | | |
|---|---|---|---|
| 6,618,612 B1 | 9/2003 | Acker | |
| 6,690,963 B2 | 2/2004 | Ben Haim | |
| 7,756,576 B2 | 7/2010 | Levin | |
| 7,848,787 B2 | 12/2010 | Osadchy | |
| 7,869,865 B2 | 1/2011 | Govari | |
| 8,456,182 B2 | 6/2013 | Bar-Tal | |
| 2002/0065455 A1 | 5/2002 | Ben Haim | |
| 2003/0018251 A1 | 1/2003 | Solomon | |
| 2003/0120150 A1 | 6/2003 | Govari | |
| 2004/0068178 A1 | 4/2004 | Govari | |
| 2007/0060832 A1 | 3/2007 | Levin | |
| 2009/0192505 A1* | 7/2009 | Askew | A61M 16/0463 424/9.4 |
| 2010/0268059 A1* | 10/2010 | Ryu | A61N 1/3627 600/407 |
| 2011/0295094 A1* | 12/2011 | Doyle | A61B 5/14551 600/340 |
| 2012/0016251 A1* | 1/2012 | Zhang | A61B 5/14503 600/532 |
| 2014/0018788 A1* | 1/2014 | Engelman | A61B 18/1492 606/33 |
| 2015/0105701 A1 | 4/2015 | Mayer | |
| 2016/0374710 A1* | 12/2016 | Sinelnikov | A61B 17/2202 600/439 |
| 2018/0199990 A1 | 7/2018 | Monir | |

* cited by examiner

RESPIRATION CONTROL DURING CARDIAC ABLATION

FIELD OF THE INVENTION

The present invention relates generally to invasive medical procedures, and specifically to cardiac ablation.

BACKGROUND

Ablation of cardiac tissue, which is used, for example, to treat cardiac arrhythmias, is complicated by the fact that the heart is not a stationary object, and any device used for the ablation has to contend with the heart's motion.

For example, U. S. Patent Application 2003/0018251 to Solomon provides a system for superimposing the position and orientation of a device on a previously acquired three-dimensional anatomic image such as a CT or MRI image, so as to enable navigation of the device to a desired location. A plurality of previously acquired three-dimensional images may be utilized to form a "movie" of a beating heart, and these can be synchronized with a patient's EKG in the operating room, and the position of the device can be superimposed on the synchronized "movie" of the beating heart.

SUMMARY

An exemplary embodiment of the present invention provides a method for invasive cardiac treatment, comprising:
inserting a catheter via a transvascular route into a beating heart of a patient who is anesthetically paralyzed and intubated for ventilation;
after inserting the catheter, temporarily halting ventilation of the patient;
moving the catheter between a plurality of locations of myocardial tissue of the heart while the ventilation is halted; and ablating the myocardial tissue of the heart at the plurality of locations while the ventilation is halted.

In a disclosed exemplary embodiment, the method includes measuring an oxygen level and a carbon dioxide level of the patient, and ensuring that the oxygen level and the carbon dioxide level are within acceptable limits when ablating tissue while the ventilation is halted. The method may also include halting ablation and resuming ventilation of the patient when the oxygen level and the carbon dioxide level are not within the acceptable limits.

In another disclosed exemplary embodiment, the catheter is selected from one of a balloon, a basket, a lasso, a focal, and a multi-spline catheter.

In a further disclosed exemplary embodiment, the catheter includes an electrode, and ablating the myocardial tissue consists of ablating the tissue with radio-frequency energy, injected into the tissue via the electrode, configured to cause cell necrosis.

In a yet further disclosed exemplary embodiment, the catheter includes an electrode, and ablating the myocardial tissue consists of ablating the tissue with radio-frequency energy, injected into the tissue via the electrode, configured to cause irreversible electroporation so as to cause cell apoptosis.

In an alternative exemplary embodiment, the catheter includes a magnetic position sensor, and inserting the catheter consists of tracking a position of the catheter within the beating heart using the magnetic position sensor.

In another alternative exemplary embodiment, the catheter includes an electrode, and inserting the catheter consists of tracking a position of the catheter within the beating heart in response to at least one of currents traversing the electrode and impedances measured between the electrode and conducting patches positioned on the patient.

In a further alternative exemplary embodiment, the method includes measuring an oxygen level of the patient, and increasing the oxygen level using the ventilation prior to halting the ventilation.

In a yet further alternative exemplary embodiment, ablating the myocardial tissue of the heart at a given location of the plurality of locations includes ablating the tissue at the given location for up to 4 seconds.

Ablating the myocardial tissue of the heart at the plurality of locations may consist of ablating the tissue at the plurality of locations for up to 4 minutes.

There is further provided, according to an exemplary embodiment of the present invention, apparatus for invasive cardiac treatment, including:
a ventilator, which is configured to supply ventilation to a patient who is anesthetically paralyzed and intubated;
a catheter, which is configured to be inserted via a transvascular route into a beating heart of the patient and to be moved between a plurality of locations of myocardial tissue of the heart while the ventilation is halted; and
a power source, which is configured to ablate myocardial tissue of the heart at the plurality of locations while the ventilation is halted.

There is further provided, according to an embodiment of the present invention, a method for invasive cardiac treatment, including:
inserting a catheter via a transvascular route into a beating heart of a patient who is anesthetically paralyzed and intubated for ventilation;
after inserting the catheter, temporarily inducing hyperventilation in the patient;
moving the catheter between a plurality of locations of myocardial tissue of the heart while the hyperventilation is induced; and
ablating the myocardial tissue of the heart at the plurality of locations while the hyperventilation is induced.

There is further provided, according to an exemplary embodiment of the present invention, apparatus for invasive cardiac treatment, including:
a ventilator, which is configured to supply ventilation to a patient who is anesthetically paralyzed and intubated;
a catheter, which is configured to be inserted via a transvascular route into a beating heart of the patient and to be moved between a plurality of locations of myocardial tissue of the heart while the ventilator induces hyperventilation in the patient; and
a power source, which is configured to ablate myocardial tissue of the heart at the plurality of locations while the hyperventilation is induced.

BRIEF DESCRIPTION OF THE DRAWINGS

The present invention will be more fully understood from the following detailed description of the exemplary embodiments thereof, taken together with the drawings in which.

DETAILED DESCRIPTION OF EXEMPLARY EMBODIMENTS

Overview

Radio-frequency (RF) ablation of tissue in the heart relies on good contact between an ablation electrode and the tissue being ablated. However, the contact is complicated by the fact that the tissue is not stationary. The tissue moves because of the beating of the heart, and also because of the patient breathing. While catheter positioning may be configured to reduce the effects of the two motions on the electrode-tissue contact, it may not completely nullify the effects of the motions.

Exemplary embodiments of the present invention effectively nullify the breathing motion during ablation as follows. A catheter is inserted into a beating heart of a patient who is anesthetically paralyzed and intubated for ventilation. The ventilation is temporarily halted, and the catheter is moved to a plurality of locations within the heart. Ablation is then performed at the plurality of locations.

Exemplary embodiments of the present invention use the fact that each ablation where RF is injected may typically be for approximately four seconds or even less. In some exemplary embodiments, prior to an ablation procedure, the patient may be ventilated to bring the patient oxygen level up, and the ventilation is switched off. The ablation procedure is then performed, and while it is being performed, the patient $O_2$ and $CO_2$ levels are monitored. So long as the $O_2$ and $CO_2$ levels remain within permissible limits, which is typically the case because the patient is comatose, ablation is continued.

By temporarily stopping patient breathing during ablation, the catheter is much more stable. In some cases a complete set of ablations may be performed, without the need for switching the ventilation back on.

In an alternative exemplary embodiment of the present invention, rather than switching ventilation off, hyperventilation is induced in the patient. The hyperventilation causes motion of the catheter due to breathing to be shallow and at a high frequency, so that any such motion can be easily filtered.

DETAILED DESCRIPTION

Figure 1:
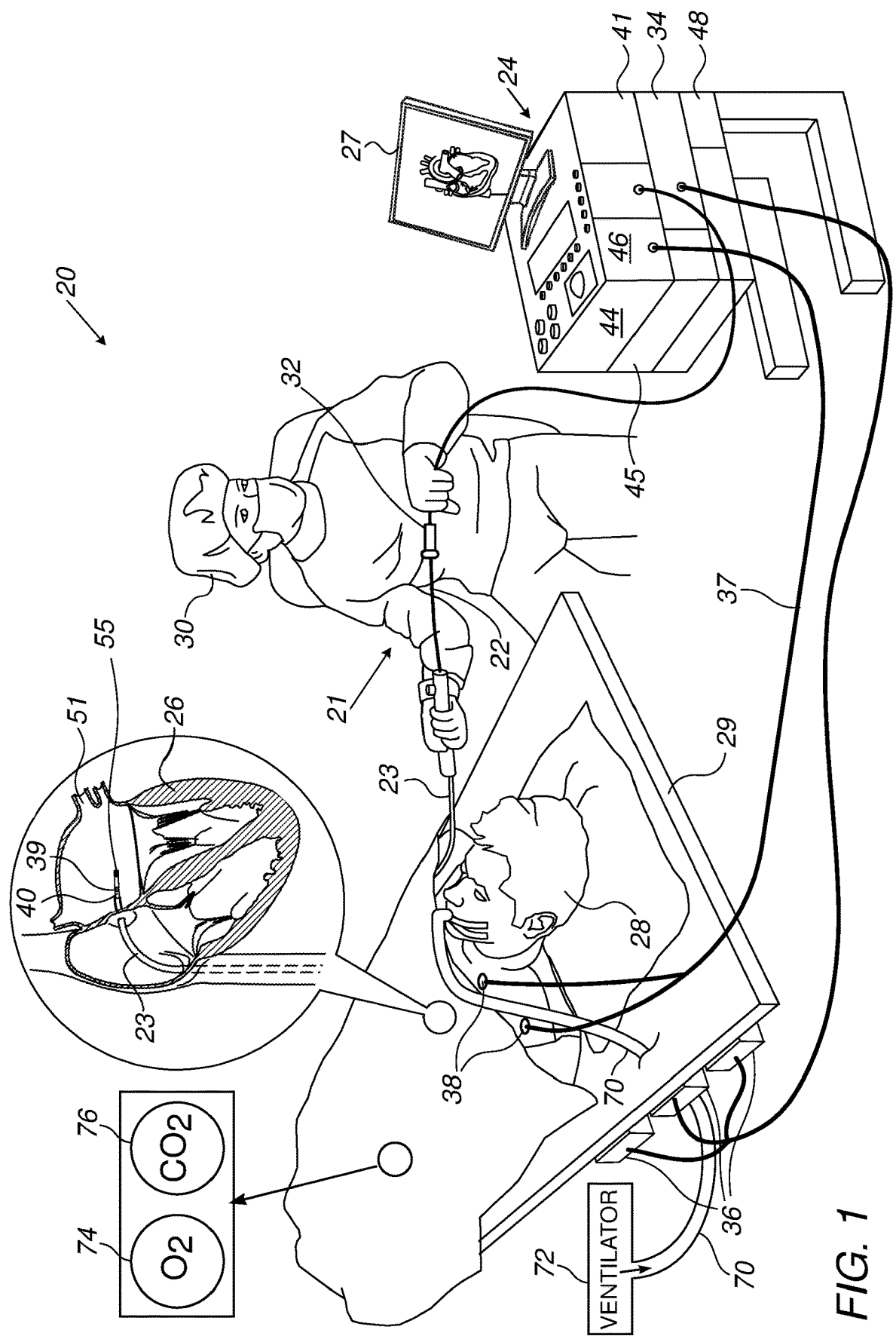
FIG. 1 is a schematic, pictorial illustration of a system for cardiac ablation, according to an exemplary embodiment of the present invention.

FIG. 1 is a schematic, pictorial illustration of a catheter-based system 20 for ablation of the heart, according to an exemplary embodiment of the present invention. System 20 comprises a focal catheter 21, comprising an insertion tube 22 for transvascular insertion into a beating heart 26 of a patient 28, who is shown lying on a table 29. A distal tip 40 is deployed at a distal end of insertion tube 22 (as seen in the inset in FIG. 1). In the illustrated exemplary embodiment, tip 40 is applied for a therapeutic procedure, comprising ablating tissue around an ostium 51 of a pulmonary vein in the left atrium of heart 26. To implement the ablation, tip 40 has one or more electrodes 55 disposed on a surface of the tip.

The proximal end of catheter 21 is connected to a control console 24 comprising a power source 45, which typically includes radio-frequency (RF) signal generation circuitry. Power source 45 supplies RF electrical signals via electrical wiring running through insertion tube 22 to electrodes 55 so as to ablate the tissue with which the electrodes are in contact. Depending on the voltage, frequency and power of the RF electrical signals, the ablation may be by RF energy injection to the heart tissue or by irreversible electroporation (IRE) of the heart tissue. RF energy injection causes necrosis of cells in the tissue by heating; IRE causes apoptosis of the cells. In the disclosure and in the claims, the term "ablation" is assumed to comprise either form of application of the RF signals supplied by power source 45. Additionally or alternatively, electrodes 55 may be used in electrophysiological (EP) sensing and mapping of electrical signals in heart 26.

To carry out the ablation procedure, patient 28 is first anesthetically paralyzed, intubated with a tube 70, and then ventilated with a ventilator 72. The anesthetization and ventilation may be carried out by a qualified practitioner, such as an anesthesiologist (not shown in FIG. 1). During ventilation of patient 28, the oxygen ($O_2$) and carbon dioxide ($CO_2$) levels in the patient's blood are checked by respective meters 74, 76, to ensure that they are within acceptable bounds, and that the ventilation is satisfactory. In an exemplary embodiment, the oxygen level is in an approximate range 75-100 mm Hg, and the carbon dioxide level is approximately 35-40 mm Hg.

Once the intubation described above has been performed, a physician 30 inserts a sheath 23 into heart 26 of patient 28 via a transvascular route, and then passes insertion tube 22 through the sheath. Physician 30 advances tip 40 of insertion tube 22 toward a target location in heart 26, for example, in proximity to ostium 51, by manipulating catheter 21 using a manipulator 32 near the proximal end of the catheter.

Once tip 40 of insertion tube 22 has reached the left atrium in heart 26, physician 30 retracts sheath 23, and further manipulates catheter 21 so as to navigate the tip to the target location within ostium 51 of the pulmonary vein. When tip 40 has reached the target location, electrodes 55 contact tissue around the ostium. Console 24 may verify that the electrodes are in good contact with the tissue by measuring the impedance between each of the electrodes and the tissue. Once good contact has been established, physician 30 actuates power source 45 to apply RF power to the tissue.

During this procedure, system 20 applies magnetic position sensing in tracking the location and orientation of insertion tube 22 and tip 40 within heart 26, and thus guides physician 30 in maneuvering the distal tip to the target location (within ostium 51 in the present example) and verifying that the tip is properly in place. For this purpose, as shown in the inset in FIG. 1, tip 40 of insertion tube 22 contains a magnetic position sensor 39. One or more magnetic field generators 36 are fixed in known positions in proximity to the body of patient 28, for example under bed 29 as shown in FIG. 1. A driver circuit 34 in console 24 applies drive signals to the magnetic field generators so as to produce multiple magnetic field components directed along different, respective axes.

During navigation of tip 40 in heart 26, magnetic sensor 39 outputs signals in response to the magnetic field components. Position sensing circuitry, such as a processor 41 in console 24, receives these signals via interface circuits 44, and processes the signals in order to find the location and orientation coordinates of tip 40.

Processor 41 presents the coordinates of tip 40 on a display 27, for example by superimposing a graphical representation of the tip, in the location and orientation indicated by position sensor 39, on a three-dimensional map of the heart chamber in which the tip is located.

The methods and apparatus for magnetic position sensing that are implemented in system 20 are based on those that are used in the CARTO® system, produced by Biosense Webster, Inc. (Irvine, California). The principles of operation of this sort of magnetic sensing are described in detail, for example, in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all hereby incorporated by reference herein in their entireties as though set forth in full. Alternatively or additionally, system 20 may implement other magnetic position sensing technologies that are known in the art.

Further alternatively or additionally, system 20 may implement current and/or impedance position sensing technologies, that measure the position of electrodes 55 in response to currents traversing the electrodes, and/or impedances of the electrodes, using an impedance/current measuring module 46. Module 46 is connected by a cable 37 to a plurality of conducting patches 38 positioned on the skin of patient 28. When configured in a current position measuring mode, module 46 injects current into electrodes 55, and measures the currents traversing the electrodes to patches 38. From the measured currents, a processor such as processor 41 calculates the location and orientation of electrodes 55. When configured in an impedance position measuring mode, module 46 measures impedances between electrodes 55 and patches 38. From the measured impedances, the location and orientation of electrodes 55 may be calculated.

The methods and apparatus for current or impedance position sensing that are implemented in system 20 are also based on those that are used in the CARTO® system. The principles of operation of these systems are described in detail, for example, in U.S. Pat. Nos. 7,756,576, 7,869,865, 7,848,787, and 8,456,182, whose disclosures are all hereby incorporated by reference herein in their entireties as though set forth in full.

In some exemplary embodiments, processor 41 comprises a general-purpose computer, with suitable interface circuits 44 for receiving signals from catheter 21 (including low-noise amplifiers and analog/digital converters), as well as for receiving signals from and controlling the operation of the other components of system 20. Processor 41 typically performs these functions under the control of software stored in a memory 48 of system 20. The software may be downloaded to the computer in electronic form, over a network, for example, or it may, alternatively or additionally, be provided and/or stored on non-transitory tangible media, such as magnetic, optical, or electronic memory. Additionally or alternatively, at least some of the functions of processor 41 may be carried out by dedicated or programmable hardware logic.

Figure 2:
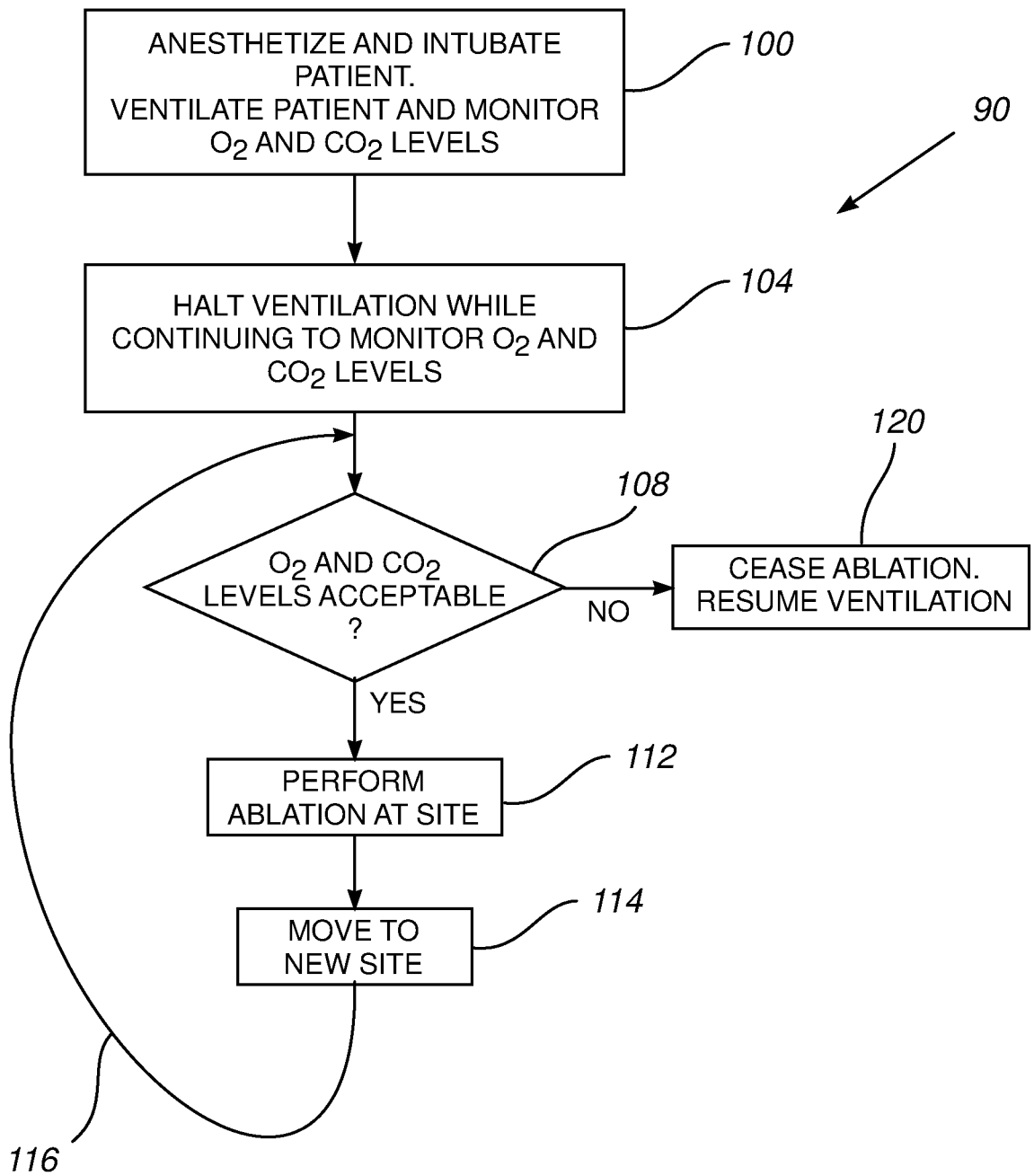
FIG. 2 is a flowchart of steps of an algorithm performed in operation of the system, according to an exemplary embodiment of the present invention.

FIG. 2 is a flowchart 90 of steps of an algorithm performed in operation of system 20, according to an exemplary embodiment of the present invention. In an initial step 100, patient 28 is prepared for an ablation procedure by being anesthetized, intubated, and ventilated as described above. In addition, as is also described above, tip 40 is inserted into patient 28 so that electrodes 55 contact desired locations of ostium 51 of heart 26. During the insertion, the ventilation of the patient is checked by monitoring the levels of $O_2$ and $CO_2$ in the patient's blood, and the ventilation is adjusted accordingly to maintain the levels at satisfactory values.

In an ablation preparatory step 104, ventilation to patient 28 is halted temporarily. Typically, prior to the halting, the ventilation is adjusted to increase the level of oxygen in the patient's blood to be close to an upper permissible bound of the oxygen level. In one embodiment the upper permissible bound is approximately 100 mm Hg. Increasing the oxygen level provides more time for ablation, described in the following steps of the flowchart, of patient 28. While ventilation is halted, both the $O_2$ and $CO_2$ levels continue to be monitored to ensure that they remain satisfactory.

In a decision step 108, while the ventilation is halted, the $O_2$ and $CO_2$ levels of patient 28 are checked to ensure they are within acceptable limits. It will be understood that after ventilation has been halted as prescribed in step 104, the decrease in $O_2$ level, and the increase in $CO_2$ level, occur at a relatively slow rate, because the patient is comatose. In one exemplary embodiment an acceptable limit for the oxygen level is greater than approximately 60 mm Hg, and an acceptable limit for the carbon dioxide level is less than approximately 45 mm Hg.

If decision step 108 returns positive, i.e., the $O_2$ and $CO_2$ levels of patient 28 are within acceptable limits, in an ablation step 112 physician 30 activates power source 45 so as to ablate the tissue at the site where electrodes 55 of tip 40 are in contact. Once the ablation has been satisfactorily executed, the physician deactivates power source 45.

On conclusion of the ablation in step 112, in a motion step 114 the physician manipulates tip 40 to move so that electrodes 55 contact a new site. Control of the flowchart then returns, as shown by arrow 116, to ablation step 112, via decision step 108, so that ablation is executed at the new site.

Exemplary embodiments of the invention continuously monitor the $O_2$ and $CO_2$ levels of patient 28, so that while decision step 108 returns positive, ablation step 112 and motion step 114 iterate.

If decision step 108 returns negative, i.e., the $O_2$ or $CO_2$ levels of patient 28 are not within acceptable limits, control continues to a ventilation step 120, wherein ventilation is resumed and ablation may be halted.

Figure 3:
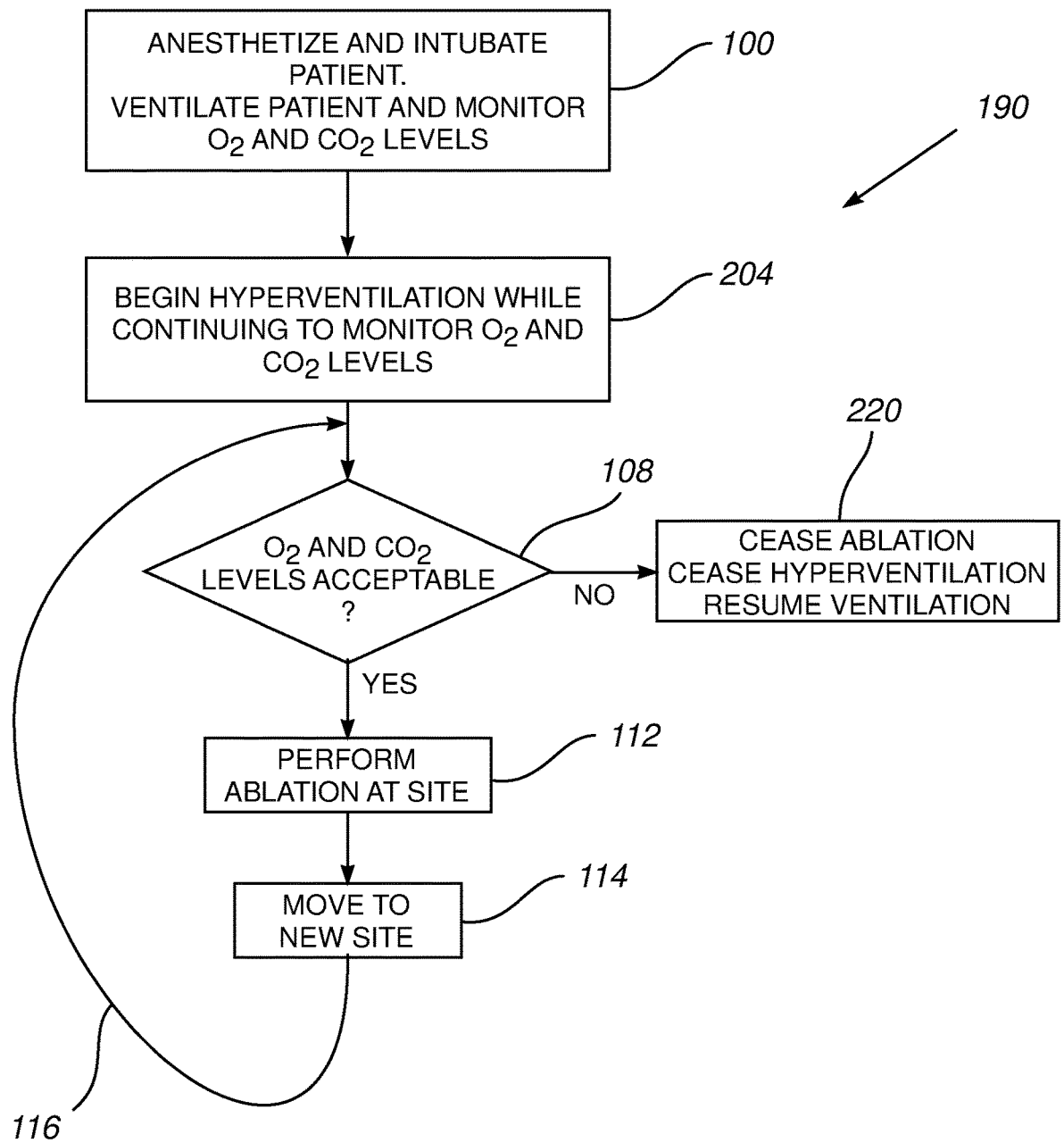
FIG. 3 is a flowchart of steps of an alternative algorithm performed in operation of the system, according to an exemplary embodiment of the present invention.

FIG. 3 is a flowchart 190 of steps of an alternative algorithm performed in operation of system 20, according to an exemplary embodiment of the present invention. Apart from the differences described below, the algorithm of flowchart 190 is generally similar to that of flowchart 90, so that the actions of steps indicated by the same reference numerals in both flowcharts are generally the same.

In flowchart 190 a hyperventilation step 204 replaces ablation preparatory step 104 of flowchart 90. In hyperventilation step 204, rather than ventilation being halted as in flowchart 90, patient 28 is hyperventilated, i.e., high frequency ventilation is induced in the patient. The high frequency ventilation may be as much as four times the regular ventilation rate, and in one embodiment the high frequency ventilation is 150 breaths/minute, or even more. While the patient is hyperventilated both the $O_2$ and $CO_2$ levels continue to be monitored to ensure that they remain satisfactory. The hyperventilation causes the patient's breathing motion to be shallow, i.e., to have a smaller amplitude than that of regular breathing or ventilation. The shallow breathing significantly improves the stability of tip 40. In addition, the low amplitude and the high frequency of the motion enable processor 41 to filter out any such motion.

In flowchart 190 a ventilation step 220 replaces ventilation step 120 in flowchart 90. Ventilation step 220 is invoked when decision 108 returns negative, and the step comprises ceasing hyperventilation and resuming normal ventilation.

Reviewing both flowcharts, in some exemplary embodiments the time for each ablation step 112, i.e., the time during which power source 45 is activated, may be as low as approximately four seconds. Assuming a moving time of approximately six seconds, the time for ablating one site and moving to another site, comprising one pass of steps 112 and 114, is of the order of approximately 10 s. The time during which steps 112 and 114 iterate may typically be up to approximately four minutes overall, since patient 28 is comatose. Thus, embodiments of the present invention enable a physician to implement ablation accurately at multiple locations, such as around ostium 51, and even to move tip 40 to one or more alternative locations such as another ostium, and perform ablations at each of the alternative locations.

The description above has assumed that ablation is performed using a focal catheter. However, the principles of the present invention may similarly be applied, mutatis mutandis, to other types of catheters such as lasso, basket, balloon, and/or multi-spline catheters having one or more electrodes suitable for ablation. It will also be appreciated that embodiments of the present invention are not just directed for use on a particular region of a heart, but may be applied, mutatis mutandis, to any region of or around a beating heart.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for invasive cardiac treatment, comprising: (a) inserting a catheter via a transvascular route into a beating heart of a patient who is anesthetically paralyzed and intubated for ventilation prior to ablation; (b) causing, by a processor of a computing system, ventilation to the patient to increase a level of oxygen in the patient prior to ablation of the patient's myocardial heart tissue; (c) monitoring, continuously, by the processor, oxygen and carbon dioxide levels of the patient; (d) causing, by the processor, ventilation of the patient to be temporarily halted prior to ablation; (e) causing, by the processor, a power source to be activated to ablate myocardial tissue at one or more locations of the heart while the ventilation is temporarily halted and while the monitored oxygen and carbon dioxide levels of the patient are within acceptable limits; (f) causing, by the processor, the power source to be deactivated to cease ablation at any of the one or more locations when the monitored oxygen and carbon dioxide levels of the patient are not within acceptable limits; (g) resuming, by the processor, ventilation until the monitored levels of oxygen and carbon dioxide are within acceptable limits; and (h) repeating, by the processor, steps (c)-(g) until the invasive cardiac treatment is complete.

2. The method according to claim 1, wherein the catheter is selected from one of a balloon, a basket, a lasso, a focal, and a multi-spline catheter.

3. The method according to claim 1, wherein the catheter comprises an electrode, and wherein ablating the myocardial tissue comprises ablating the tissue with radio-frequency energy, injected into the tissue via the electrode, configured to cause cell necrosis.

4. The method according to claim 1, wherein the catheter comprises an electrode, and wherein ablating the myocardial tissue comprises ablating the tissue with radio-frequency energy, injected into the tissue via the electrode, configured to cause irreversible electroporation so as to cause cell apoptosis.

5. The method according to claim 1, wherein the catheter comprises a magnetic position sensor, and wherein inserting the catheter comprises tracking a position of the catheter within the beating heart using the magnetic position sensor.

6. The method according to claim 1, wherein the catheter comprises an electrode, and wherein inserting the catheter comprises tracking a position of the catheter within the beating heart in response to at least one of currents traversing the electrode and impedances measured between the electrode and conducting patches positioned on the patient.

7. The method according to claim 1, wherein ablating the myocardial tissue of the heart at the none or more locations comprises ablating the tissue at the one or more locations for up to 4 seconds.

8. The method according to claim 1, wherein ablating the myocardial tissue of the heart at the one or more locations comprises ablating the tissue at the one or more locations for up to 4 minutes.

9. Apparatus for invasive cardiac treatment, comprising:
one or more processors; and
a non-transitory computer readable medium storing a plurality of instructions, which when executed, cause the one or more processors to:
(a) cause a supply of ventilation from a ventilator to a patient to be adjusted to increase a level of oxygen in the patient prior to ablation of the patient's myocardial heart tissue using a catheter that has been inserted via a transvascular route into the heart of the patient,
(b) cause oxygen and carbon dioxide levels of the patient to be monitored continuously,
(c) cause ventilation of the patient prior to ablation to be halted temporarily,
(d) cause a power source to be activated to ablate myocardial tissue at one or more locations of the heart while the ventilation is temporarily halted and while the monitored levels of oxygen and carbon dioxide are within acceptable limits,
(e) cause the power source to be deactivated to cease ablation at the one or more locations when monitored oxygen and carbon dioxide levels are not within acceptable limits,
(f) cause ventilation to be resumed until the monitored levels of oxygen and carbon dioxide are within acceptable limits, and
(g) repeat steps (c)-(f) until the invasive cardiac treatment is complete.

10. The apparatus according to claim 9, and comprising meters configured to measure the oxygen level and the carbon dioxide level of the patient.

11. The apparatus according to claim 9, wherein the catheter is selected from one of a balloon, a basket, a lasso, a focal, and a multi-spline catheter.

12. The apparatus according to claim 9, wherein the catheter comprises an electrode, and wherein ablating the myocardial tissue comprises ablating the tissue with radio-frequency energy, injected into the tissue via the electrode, configured to cause cell necrosis.

13. The apparatus according to claim 9, wherein the catheter comprises an electrode, and wherein ablating the myocardial tissue comprises ablating the tissue with radio-frequency energy, injected into the tissue via the electrode, configured to cause irreversible electroporation so as to cause cell apoptosis.

14. The apparatus according to claim 9, wherein the catheter comprises a magnetic position sensor, and wherein inserting the catheter comprises tracking a position of the catheter within the beating heart using the magnetic position sensor.

15. The apparatus according to claim 9, wherein the catheter comprises an electrode, and wherein inserting the catheter comprises tracking a position of the catheter within the beating heart in response to at least one of currents traversing the electrode and impedances measured between the electrode and conducting patches positioned on the patient.

16. The apparatus according to claim 9, and comprising a meter configured to measure the oxygen level of the patient, and wherein the plurality of instructions further cause the one or more processors to increase the oxygen level using the ventilation prior to halting the ventilation.

17. The apparatus according to claim 9, wherein ablating the myocardial tissue of the heart at the one or more locations comprises ablating the tissue at the one or more locations for up to 4 seconds.

18. The apparatus according to claim 9, wherein ablating the myocardial tissue of the heart at the one or more locations comprises ablating the tissue at the one or more locations for up to 4 minutes.

\* \* \* \* \*